(12) United States Patent
Guedon

(10) Patent No.: US 8,539,988 B2
(45) Date of Patent: Sep. 24, 2013

(54) DEVICE FOR THE TRANSFER OF A MEDIUM

(75) Inventor: Pierre Guedon, Rosheim (FR)

(73) Assignee: EMD Millipore Corporation, Billerica, MA (US)

( * ) Notice: Subject to any disclaimer, the term of this patent is extended or adjusted under 35 U.S.C. 154(b) by 820 days.

(21) Appl. No.: 12/638,283

(22) Filed: Dec. 15, 2009

(65) Prior Publication Data

US 2010/0154569 A1    Jun. 24, 2010

(30) Foreign Application Priority Data

Dec. 18, 2008    (FR) ...................................... 08 58805

(51) Int. Cl.
*B65B 3/00*    (2006.01)
*G01N 1/10*    (2006.01)

(52) U.S. Cl.
USPC .......... 141/21; 141/375; 141/384; 73/863.31; 73/863.84

(58) Field of Classification Search
USPC ............. 141/18, 21, 368–369, 375, 383–384, 141/392; 73/863.31, 863.81, 863.86
See application file for complete search history.

(56) References Cited

U.S. PATENT DOCUMENTS

| | | |
|---|---|---|
| 214,367 A | 4/1879 | Colvin |
| 988,378 A | 4/1911 | Olson |
| 1,503,132 A | 7/1924 | Prator |
| 1,585,163 A | 5/1926 | Milner |
| 1,831,457 A | 11/1931 | Larsen |
| 1,852,445 A | 4/1932 | Calkins et al. |
| 2,012,836 A | 8/1935 | Talbot et al. |
| 2,122,991 A | 7/1938 | Polston |
| 2,240,888 A | 5/1941 | Hageline |
| 2,426,808 A | 9/1947 | Auer |

(Continued)

FOREIGN PATENT DOCUMENTS

| | | |
|---|---|---|
| CN | 101022875 A | 8/2007 |
| DE | 2161702 | 6/1973 |

(Continued)

OTHER PUBLICATIONS

The French Search Report in a co-pending foreign application (FR 0858804) dated Nov. 13, 2009.

(Continued)

*Primary Examiner* — Gregory Huson
*Assistant Examiner* — Nicolas A Arnett
(74) *Attorney, Agent, or Firm* — Nields, Lemack & Frame, LLC

(57) ABSTRACT

The device for the transfer of a medium comprises a magazine having two main faces (17) of which one is adapted to cooperate with a container and a lateral face (18) extending between said main faces (17) as well as at least one sliding valve (3) housed in a cavity of said magazine (2) and in which there is formed a transfer duct (59) for said medium which issues on said face (17) adapted to cooperate with said container, said valve (3) having a closed position in which it sealingly isolates said duct (59) from said container and an open position in which said duct (59) is placed in communication with said container; said valve (3) comprising a valve member (40), an isolation sleeve (41) surrounding at least partially said valve member (40) as well as spring means (58) adapted to be compressed by said valve member (40) when said valve (3) is in its open position.

28 Claims, 6 Drawing Sheets

(56) References Cited

U.S. PATENT DOCUMENTS

| | | |
|---|---|---|
| 2,642,256 A | 6/1953 | Stehlin |
| 2,712,881 A | 7/1955 | Mathisen |
| 2,736,201 A | 2/1956 | Ohlsen et al. |
| 2,767,587 A | 10/1956 | Perkins |
| 2,776,473 A | 1/1957 | Dailey et al. |
| 2,779,350 A | 1/1957 | Owens |
| 2,844,964 A | 7/1958 | Guibert |
| 2,859,932 A | 11/1958 | Mackal |
| 2,865,394 A | 12/1958 | Presley |
| 2,872,817 A | 2/1959 | Pitts |
| 2,952,269 A | 9/1960 | Stehlin |
| 2,994,224 A | 8/1961 | Brown |
| 3,038,485 A | 6/1962 | Hosek |
| 3,039,482 A | 6/1962 | Goldberg |
| 3,097,532 A | 7/1963 | Brown et al. |
| 3,219,047 A | 11/1965 | Kircher, III et al. |
| 3,223,100 A | 12/1965 | Koenig et al. |
| 3,244,376 A | 4/1966 | Thompson |
| 3,260,120 A | 7/1966 | Stilwell |
| 3,276,447 A | 10/1966 | Hamilton et al. |
| 3,319,622 A | 5/1967 | Shiner |
| 3,390,677 A | 7/1968 | Razimbaud |
| 3,424,181 A | 1/1969 | Morse |
| 3,479,880 A | 11/1969 | Mutter et al. |
| 3,525,350 A | 8/1970 | Hosek |
| 3,621,719 A | 11/1971 | Goodman et al. |
| 3,633,621 A | 1/1972 | Myers |
| 3,638,499 A | 2/1972 | Saint-Andre |
| 3,678,959 A | 7/1972 | Liposky |
| 3,696,932 A | 10/1972 | Rosenberg |
| 3,736,099 A | 5/1973 | Begg et al. |
| 3,747,411 A | 7/1973 | McDermott et al. |
| 3,776,042 A | 12/1973 | Werra et al. |
| 3,779,082 A | 12/1973 | Galloway |
| 3,802,782 A | 4/1974 | Natelson |
| 3,848,581 A | 11/1974 | Cinqualbre et al. |
| 3,858,449 A | 1/1975 | Singer |
| 3,921,456 A | 11/1975 | Newcomb, Jr. et al. |
| 3,985,332 A | 10/1976 | Walker |
| 4,015,631 A | 4/1977 | Hayes |
| 4,018,059 A | 4/1977 | Hatch |
| 4,034,775 A | 7/1977 | Slagel |
| 4,055,179 A | 10/1977 | Manschot et al. |
| 4,061,709 A | 12/1977 | Miller et al. |
| 4,064,003 A | 12/1977 | Newton |
| 4,094,197 A | 6/1978 | Harris, Sr. et al. |
| 4,207,922 A | 6/1980 | Andrieux et al. |
| 4,244,224 A | 1/1981 | Conn |
| 4,294,247 A | 10/1981 | Carter et al. |
| 4,296,759 A | 10/1981 | Joslin et al. |
| 4,325,401 A | 4/1982 | Ukai et al. |
| 4,346,609 A | 8/1982 | Diesel |
| 4,353,386 A | 10/1982 | Slagel |
| 4,378,824 A | 4/1983 | Carder, Sr. |
| 4,423,641 A | 1/1984 | Ottung |
| 4,423,642 A | 1/1984 | Kuboichi |
| 4,454,772 A | 6/1984 | Brunner et al. |
| 4,458,543 A | 7/1984 | Mieth |
| 4,479,393 A | 10/1984 | Shores |
| 4,525,127 A | 6/1985 | Welker |
| 4,527,436 A | 7/1985 | Jones |
| 4,537,593 A | 8/1985 | Alchas |
| 4,557,151 A | 12/1985 | Welker |
| 4,569,236 A | 2/1986 | Kitchen et al. |
| 4,580,452 A | 4/1986 | Masson |
| 4,584,887 A | 4/1986 | Galen |
| 4,587,856 A | 5/1986 | Otis |
| 4,587,887 A | 5/1986 | Shibayama et al. |
| 4,622,457 A | 11/1986 | Bradley et al. |
| 4,630,847 A | 12/1986 | Blenkush |
| 4,657,027 A | 4/1987 | Paulsen |
| 4,669,312 A | 6/1987 | Maurer |
| 4,669,321 A | 6/1987 | Meyer |
| 4,704,910 A | 11/1987 | Conrad |
| 4,826,055 A | 5/1989 | Stull |
| 4,836,236 A | 6/1989 | Ladisch |
| 4,838,877 A | 6/1989 | Massau |
| 4,861,239 A | 8/1989 | Simmons et al. |
| 4,913,185 A | 4/1990 | Mattei |
| 4,941,517 A | 7/1990 | Galloway |
| 4,942,901 A | 7/1990 | Vescovini |
| 4,944,875 A | 7/1990 | Gaignet |
| 4,997,108 A | 3/1991 | Hata |
| 5,058,619 A | 10/1991 | Zheng |
| 5,095,765 A | 3/1992 | Filbey et al. |
| 5,117,872 A | 6/1992 | Yie |
| 5,158,558 A | 10/1992 | Melker et al. |
| 5,161,417 A | 11/1992 | Strong et al. |
| 5,177,872 A | 1/1993 | Lewis et al. |
| 5,246,204 A | 9/1993 | Ottung |
| 5,285,999 A | 2/1994 | Scholz |
| 5,296,197 A | 3/1994 | Newberg et al. |
| 5,360,413 A | 11/1994 | Leason et al. |
| 5,375,477 A | 12/1994 | Neill et al. |
| 5,398,557 A | 3/1995 | Shimizu et al. |
| 5,435,339 A | 7/1995 | Hayes |
| 5,452,746 A | 9/1995 | Hoobyar et al. |
| 5,463,908 A | 11/1995 | Rosolia |
| 5,468,388 A | 11/1995 | Goddard et al. |
| 5,474,546 A | 12/1995 | Ambrisco et al. |
| D366,935 S | 2/1996 | Arthun et al. |
| 5,520,218 A | 5/1996 | Hlavinka et al. |
| 5,525,301 A | 6/1996 | Newberg et al. |
| 5,533,983 A | 7/1996 | Haining |
| 5,535,635 A | 7/1996 | Shaw |
| 5,542,305 A | 8/1996 | Hollinger |
| 5,549,568 A | 8/1996 | Shields |
| 5,585,576 A | 12/1996 | Jaeger |
| D381,067 S | 7/1997 | Karmalm |
| 5,730,418 A | 3/1998 | Feith et al. |
| 5,747,708 A | 5/1998 | Weiberth |
| 5,755,155 A | 5/1998 | Buesing |
| 5,766,462 A | 6/1998 | Jones |
| 5,786,209 A | 7/1998 | Newberg |
| 5,820,614 A | 10/1998 | Erskine et al. |
| 5,829,425 A | 11/1998 | Woods et al. |
| 5,868,433 A | 2/1999 | Matkovich |
| 5,885,255 A | 3/1999 | Jaeger, Jr. et al. |
| 5,897,526 A | 4/1999 | Vaillancourt |
| 5,911,252 A | 6/1999 | Cassell |
| 5,948,998 A | 9/1999 | Witte et al. |
| 6,009,684 A | 1/2000 | Buesing |
| 6,030,578 A | 2/2000 | McDonald |
| 6,032,543 A | 3/2000 | Arthun et al. |
| 6,068,617 A | 5/2000 | Richmond |
| 6,096,011 A | 8/2000 | Trombley, III et al. |
| 6,133,022 A | 10/2000 | Newberg et al. |
| 6,145,810 A | 11/2000 | Connolly et al. |
| 6,156,025 A | 12/2000 | Niedospial, Jr. et al. |
| 6,162,206 A | 12/2000 | Bindokas et al. |
| 6,170,800 B1 | 1/2001 | Meloul et al. |
| 6,196,522 B1 | 3/2001 | Yuen et al. |
| 6,210,372 B1 | 4/2001 | Tessmann et al. |
| 6,221,041 B1 | 4/2001 | Russo |
| 6,237,639 B1 | 5/2001 | Jougla et al. |
| 6,254,773 B1 | 7/2001 | Biltoft |
| 6,273,869 B1 | 8/2001 | Vaillancourt |
| 6,306,191 B1 | 10/2001 | McInerney et al. |
| 6,314,987 B1 | 11/2001 | Hay |
| 6,345,640 B1 | 2/2002 | Newberg et al. |
| 6,345,645 B1 | 2/2002 | Kenna et al. |
| D454,173 S | 3/2002 | Almasian et al. |
| 6,354,466 B1 | 3/2002 | Karpisek |
| 6,357,306 B1 | 3/2002 | Jaeger |
| 6,360,794 B1 | 3/2002 | Turner |
| 6,386,137 B1 | 5/2002 | Riche |
| 6,390,127 B2 | 5/2002 | Schick |
| 6,477,906 B1 | 11/2002 | Peterson |
| 6,516,677 B1 | 2/2003 | Suter |
| 6,558,365 B2 | 5/2003 | Zinger et al. |
| 6,568,844 B1 | 5/2003 | Arthun et al. |
| 6,601,823 B2 | 8/2003 | Newberg |
| 6,623,631 B1 | 9/2003 | Graus et al. |
| 6,648,006 B1 | 11/2003 | Ostergaard |

| | | | | | | |
|---|---|---|---|---|---|---|
| 6,672,561 B2 | 1/2004 | Kerg et al. | | EP | 0107579 A2 | 5/1984 |
| 6,699,229 B2 | 3/2004 | Zinger et al. | | EP | 0154002 A1 | 9/1985 |
| 6,715,624 B2 | 4/2004 | Brockwell | | EP | 0508749 A2 | 10/1992 |
| 6,779,575 B1 | 8/2004 | Arthun | | EP | 0510355 A1 | 10/1992 |
| 6,860,162 B1 | 3/2005 | Jaeger | | EP | 0576380 A1 | 12/1993 |
| 6,871,669 B2 | 3/2005 | Meyer et al. | | EP | 0468957 B1 | 6/1994 |
| 6,902,144 B2 | 6/2005 | de Cler | | EP | 0684050 A2 | 11/1995 |
| 6,916,012 B2 | 7/2005 | Newberg | | EP | 0691492 A1 | 1/1996 |
| 7,137,974 B2 | 11/2006 | Almasian et al. | | EP | 1008359 A1 | 6/2000 |
| 7,195,181 B2 | 3/2007 | Steingass et al. | | EP | 1 231 699 A1 | 8/2002 |
| 7,272,981 B2 | 9/2007 | Bigalke | | EP | 1321699 A2 | 6/2003 |
| 7,273,550 B2 | 9/2007 | Gutman et al. | | EP | 1 329 210 A1 | 7/2003 |
| 7,293,475 B2 | 11/2007 | Furey et al. | | EP | 1548420 A2 | 6/2005 |
| 7,293,477 B2 | 11/2007 | Furey et al. | | EP | 1370788 B1 | 11/2005 |
| 7,350,535 B2 | 4/2008 | Liepold et al. | | EP | 0858589 B1 | 12/2005 |
| 7,473,360 B2 | 1/2009 | Hoffman et al. | | EP | 1 499 382 B1 | 12/2006 |
| 7,488,446 B2 | 2/2009 | Meyer et al. | | EP | 1 962 076 A2 | 8/2008 |
| 7,578,205 B2 | 8/2009 | Belongia | | FR | 2023259 A | 8/1970 |
| 7,578,936 B2 | 8/2009 | Gaignet et al. | | GB | 943132 | 11/1963 |
| 7,597,683 B2 | 10/2009 | Myhrberg et al. | | GB | 1381391 | 1/1975 |
| RE41,169 E | 3/2010 | Arthun | | GB | 1418046 | 12/1975 |
| 7,722,733 B2 | 5/2010 | Tomasetti et al. | | GB | 1463303 | 2/1977 |
| 7,753,340 B2 | 7/2010 | Liepold et al. | | GB | 1479226 | 7/1977 |
| 7,815,362 B2 | 10/2010 | Myhrberg et al. | | GB | 1511240 | 5/1978 |
| 7,921,740 B2 | 4/2011 | Furey et al. | | GB | 1573482 | 8/1980 |
| 7,927,316 B2 | 4/2011 | Proulx et al. | | GB | 2327369 A | 1/1999 |
| 7,959,754 B2 | 6/2011 | Arthun | | GB | 2365511 A | 2/2002 |
| 8,029,023 B2 | 10/2011 | Arthun et al. | | JP | 42-15498 U | 9/1967 |
| 8,167,480 B2 | 5/2012 | Myhrberg et al. | | JP | 44-4942 U | 2/1969 |
| 8,281,961 B2 * | 10/2012 | Martin .................... 222/482 | | JP | 49-112631A U | 9/1974 |
| 2002/0129858 A1 | 9/2002 | Meyer et al. | | JP | 58-131802 U | 9/1983 |
| 2003/0188588 A1 | 10/2003 | Jaeger | | JP | 59-38278A U | 3/1984 |
| 2005/0016620 A1 | 1/2005 | Proulx et al. | | JP | 2-52667 A | 2/1990 |
| 2005/0035597 A1 | 2/2005 | Bamberger et al. | | JP | 2-71728 A | 3/1990 |
| 2005/0090797 A1 | 4/2005 | Almasian et al. | | JP | 02-118276 A | 5/1990 |
| 2005/0132821 A1 | 6/2005 | Furey et al. | | JP | 2-121679 U | 10/1990 |
| 2005/0150546 A1 | 7/2005 | Liepold et al. | | JP | 3-141948 A | 6/1991 |
| 2005/0285066 A1 | 12/2005 | Huang | | JP | 6-010845 U | 2/1994 |
| 2006/0081804 A1 | 4/2006 | Cong | | JP | 6-23045 A | 2/1994 |
| 2006/0086922 A1 | 4/2006 | Jensen et al. | | JP | 6-327772 A | 11/1994 |
| 2006/0091060 A1 | 5/2006 | Gutman et al. | | JP | 7-51371 A | 2/1995 |
| 2006/0142730 A1 | 6/2006 | Proulx et al. | | JP | 8-502339 A | 3/1996 |
| 2006/0201263 A1 | 9/2006 | Furey et al. | | JP | 8-168535 A | 7/1996 |
| 2006/0211995 A1 | 9/2006 | Myhrberg et al. | | JP | 9-154945 A | 6/1997 |
| 2006/0243942 A1 | 11/2006 | Liepold et al. | | JP | 9-512892 A | 12/1997 |
| 2006/0272432 A1 | 12/2006 | Belongia | | JP | 11-141713 A | 5/1999 |
| 2007/0106264 A1 | 5/2007 | Proulx et al. | | JP | 11-270705 A | 10/1999 |
| 2007/0193375 A1 | 8/2007 | Pandori et al. | | JP | 11-514741 A | 12/1999 |
| 2007/0253287 A1 | 11/2007 | Myhrberg et al. | | JP | 2000-55792 A | 2/2000 |
| 2008/0000820 A1 | 1/2008 | Mitchell | | JP | 2001-170188 A | 6/2001 |
| 2008/0022785 A1 | 1/2008 | Furey et al. | | JP | 2001-269401 A | 10/2001 |
| 2008/0087860 A1 | 4/2008 | Vaillancourt et al. | | JP | 2001-523525 A | 11/2001 |
| 2008/0103476 A1 | 5/2008 | Schulte | | JP | 2002-510996 A | 4/2002 |
| 2008/0185552 A1 | 8/2008 | Myhrberg et al. | | JP | 2004-332797 A | 11/2004 |
| 2008/0277878 A1 | 11/2008 | Arthun et al. | | JP | 2005-181336 A | 7/2005 |
| 2009/0019952 A1 | 1/2009 | Furey et al. | | JP | 2005-519825 A | 7/2005 |
| 2009/0054758 A1 | 2/2009 | Dunseath | | JP | 2006-166723 A | 7/2006 |
| 2009/0101575 A1 | 4/2009 | Alburty et al. | | JP | 2008-185218 A | 8/2008 |
| 2009/0229671 A1 | 9/2009 | Hartnett et al. | | JP | 2009-2965 A | 1/2009 |
| 2009/0250157 A1 | 10/2009 | Arthun | | JP | 2009-192540 A | 8/2009 |
| 2010/0123094 A1 | 5/2010 | Zumbrum | | JP | 4332106 B2 | 9/2009 |
| 2010/0133459 A1 | 6/2010 | Zumbrum | | SU | 649954 | 2/1979 |
| 2010/0158759 A1 | 6/2010 | Olivier | | WO | 86/02450 A1 | 4/1986 |
| 2010/0290311 A1 | 11/2010 | Myhrberg et al. | | WO | 90/12972 A1 | 11/1990 |
| 2010/0326212 A1 | 12/2010 | Furey et al. | | WO | 91/00215 A1 | 1/1991 |
| 2011/0155258 A1 | 6/2011 | Zumbrum | | WO | 94/08173 A1 | 4/1994 |
| 2011/0155274 A1 | 6/2011 | Zumbrum | | WO | 94/19086 A1 | 9/1994 |
| 2011/0197989 A1 | 8/2011 | Proulx et al. | | WO | 95/30856 A1 | 11/1995 |
| 2011/0253233 A1 | 10/2011 | Hillier et al. | | WO | 96/30076 A1 | 10/1996 |
| | | | | WO | 97/16715 A1 | 5/1997 |
| FOREIGN PATENT DOCUMENTS | | | | WO | 98/45188 A1 | 10/1998 |
| DE | 3215799 A1 | 11/1983 | | WO | 98/50105 A1 | 11/1998 |
| DE | 3633431 A1 | 4/1988 | | WO | 99/03568 A1 | 1/1999 |
| DE | 3701250 A1 | 7/1988 | | WO | 99/06089 A1 | 2/1999 |
| DE | 8812723 U1 | 12/1988 | | WO | 99/26580 A1 | 6/1999 |
| DE | 100 39 196 A1 | 2/2002 | | WO | 00/78472 A1 | 12/2000 |
| DE | 6 980 7924 T2 | 1/2003 | | WO | 03/090842 A1 | 11/2003 |
| DE | 603 10 700 T2 | 10/2007 | | WO | 03/090843 A1 | 11/2003 |
| EP | 0103396 A2 | 3/1984 | | WO | 2005/012775 A1 | 2/2005 |

| | | | |
|---|---|---|---|
| WO | 2006/022816 A2 | 3/2006 |
| WO | 2006/026253 A2 | 3/2006 |
| WO | 2008/042285 A2 | 4/2008 |
| WO | 2008/048511 A2 | 4/2008 |
| WO | 2008/136720 A1 | 11/2008 |
| WO | 2010/008395 A1 | 1/2010 |
| WO | 2010/008396 A2 | 1/2010 |
| WO | 2013/011231 A1 | 1/2013 |

OTHER PUBLICATIONS

The French Search Report in a corresponding foreign application (FR 0858805) dated Nov. 20, 2009.
Notice of Allowance mailed Feb. 16, 2012 in co-pending U.S. Appl. No. 12/638,242.
Millipore's Initial Infringement Contentions, Document No. 19, filed Oct. 8, 2009 in the United States District Court for the District of Massachusetts, Civil Action No. 09-10765 DPW, 16 pages.
Gore's Preliminary Non-Infringement Contentions to Plaintiff Millipore Corporation, Document No. 20, filed Oct. 29, 2009 in the United States District Court for the District of Massachusetts, Civil Action No. 09-10765 DPW, 30 pages.
Gore's Preliminary Invalidity Contentions to Plaintiff Millipore Corporation, Document No. 21, filed Oct. 29, 2009 in the United States District Court for the District of Massachusetts, Civil Action No. 09-10765 DPW, 108 pages.
Preliminary Noninfringement and Invalidity Disclosures of Allpure Technologies, Inc., Document 22, filed Jul. 20, 2011 in the United States District Court for the District of Massachusetts, Civil Action No. 11-cv-10221-DPW, 15 pages.
Gore's First Supplemental Response to Millipore's First Set of Interrogatories [Interrogatory Nos. 11, 15 and 16] dated Nov. 1, 2011, United States District Court for the District of Delaware, Civil Action No. 11-346-SLR, 86 pages.
Gore's Third Supplemental Response to Millipore's First Set of Interrogatories [Interrogatory No. 11], Civil Action No. 11-346-SLR, United States District Court for the District of Delaware, dated Dec. 21, 2011, part 1—pp. 1-43; part 2—pp. 44-85 with Exhibits A-E (334 pages), Exhibits F-G (115 pages) and Exhibits H-I (114 pages). (Note due to the size limitations this is uploaded into 5 parts).
Memorandum and Order, Document No. 70, dated Sep. 20, 2010, in the United States District Court for the District of Massachusetts, Civil Action No. 09-10765-DPW, 59 pages.
Correspondence from T. Pender to C. Burrell dated Dec. 2, 2011 regarding C.A. No. 11-CV-346-SLR (Bates Stamp GF000001-GF000008), 8 pages.
Documents Produced by Third Party Casella Sales and Marketing Inc., Bates No. CSMI000001 through CSMI000066, 65 pages, Nov. 2011.
Allegheny Bradford Corporation's Objections and Responses to Subpoena, Civil Action No. 1:11-cv-00346-SLR, dated Dec. 15, 2011 in the USDC for the District of Delaware, and Bates # ABC00001 through Bates # ABC000012, 19 pages.
Fluid Line Technology Corporation Documents produced in *Gore* v. *Millipore*, Nov. 28, 2011, Bates # FLT000001 through Bates # FLT000103, 48 pages.
File history of U.S. Appl. No. 78/140,217, filed Jul. 1, 2002, 53 pages.
File history of U.S. Appl. No. 60/375,747, filed Apr. 26, 2002, Document 53-2, Case 1:09-cv-10765-DPW, filed May 25, 2010, 50 pages.
File history of U.S. Appl. No. 60/500,024, filed Sep. 4, 2003, 23 pages.
NovAseptic—How to Use NA sampling system, http://www.novaseptic.se/main.asp?typ=6, dated Feb. 13, 2002, 2 pages.
NovAseptic, Novaseptum Liquid Sampling System—Totally Enclosed System/ No Cross Contamination/ Presterilized Disposable Unit/ Pyrogen Free, p. 1-4, Feb. 2003.
Opticap Valve: Millipore Application Note, Jul. 2000, "Gamma Compatible Sterilizing Grade Filter Capsules for Use with Disposable Manufacturing Containers"; 6-pages.
Opticap Vent; Millipore Data Sheet, Apr. 2005, "Gamma Compatible Sterilizing-grade Durapore 0.1 um and 0.22 um Filters", 8-pages.
Opticap3; Millipore Corporation, Nov. 2001, "Opticap TM Capsules with Millistak+™. Media User Guide", 4-Pages.

Pharmenta AptiPort Sampling Valve, http://www.web.archive.org/web/20031029084907/http://www.pharmenta.com/aptiport.htm, 1 page, last modified Mar. 29, 2004, retrieved from internet May 8, 2012.
ITT, Pure-Flo Hygienic diaphragm valves, actuators, and switch packages, http://www.ittpureflo.com/valvetype.html dated May 8, 2012 and Oct. 30, 2009, 12pages.
Pure-Flo Solutions, Pure-Flo Radial Seated Tank Bottom Diaphragm Valve, Datasheet [online], ITT Industries, 2001. (2 pages).
Pure-Flo: Sample and Bleed Valves for the pharmaceutical and bioprocessing industries, dated Sep. 1992, ITT Fluid Tech. Corp., (Bates stamp WLG=DEL0003938-WLG-DEL00039394), 6 pages.
Risk Free Connection of Sterilized Single-Use Fluid Path Assemblies to Stainless Steel SIP Systems with Lynx ST (Steam-To) Connectors [online], Millipore Corporation Application Note, 2008. Retrieved from the Internet: www.millipore.com (8 pages).
Sani-Tech Globe & Angle Valve product information, dated Aug. 1989 (Bates stamp WLG-DEL00040302-WLG-DEL00040304), 3 pages.
Steam-In-Place Bag Connector, http://www.fluidcomponents.net/tc_tech.html, download on Feb. 18, 2010, 1 page.
Tingley, S., "Plastic factory, Part II: The final pieces of the disposable puzzle", Alternative Manufacturing, Clean Rooms, pp. 12-14 (Jun. 2003), 4 pages.
Tingley, S., "Plastic factory: Disposable biopharmaceutical manufacturing takes a giant leap forward", Alternative Manufacturing, Clean Rooms (Feb. 2003), 6 pages.
Valves, Gemu Valves and Distributor, Diaphragm Valves, Sanitary Valves, Aseptic Valves, Valves and Fittings, Casella Sales and Marketing, Inc., http://www.casellasales.com, dated May 8, 2012 and Oct. 30, 2009, 13 pages.
Waukesha Cherry-Burrell Manual Valves, dated May 2000 (Bates stamp CSM1000044-CSMI000066), 23 pages.
Wendt, D., "BioTrends: Disposable Processing Systems: How Suppliers Are Meeting Today's Biotech Challenges from Fluid Handling to Filtration", Biopharm International, p. 18 (Jul. 2003), 7 pages.
Office Action dated Mar. 19, 2010 in co-pending U.S. Appl. No. 12/284,666.
Notice of Allowance dated Oct. 1, 2010 in co-pending U.S. Appl. No. 12/284,666.
Supplemental Notice of Allowance dated Oct. 7, 2010 in co-pending U.S. Appl. No. 12/284,666.
Supplemental Notice of Allowance dated Oct. 15, 2010 in co-pending U.S. Appl. No. 12/284,666.
Supplemental Notice of Allowance dated Oct. 20, 2010 in co-pending U.S. Appl. No. 12/284,666.
Notice of Allowance mailed Mar. 29, 2012 in co-pending U.S. Appl. No. 12/284,666.
Miscellaneous Communication mailed Apr. 18, 2012 and Apr. 16, 2012 in co-pending U.S. Appl. No. 12/284,666.
Office Action dated Jan. 30, 2009 in co-pending U.S. Appl. No. 11/878,126.
Final Rejection dated Jun. 26, 2009 in co-pending U.S. Appl. No. 11/878,126.
Office Action dated Aug. 12, 2009 in co-pending U.S. Appl. No. 11/878,126.
Office Action dated Sep. 25, 2009 in co-pending U.S. Appl. No. 11/878,126.
Final Rejection dated Apr. 6, 2010 in co-pending U.S. Appl. No. 11/878,126.
Notices of Allowance dated Feb. 16, 2011 in co-pending U.S. Appl. No. 11/878,126.
Notice of Allowance dated Mar. 1, 2011 in co-pending U.S. Appl. No. 11/878,126.
Office Action dated Sep. 22, 2005 in co-pending U.S. Appl. No. 10/500,077.
Final Rejection dated Apr. 21, 2006 in co-pending U.S. Appl. No. 10/500,077.
Office Action dated Nov. 16, 2006 in co-pending U.S. Appl. No. 10/500,077.
Final Rejection dated Sep. 10, 2007 in co-pending U.S. Appl. No. 10/500,077.

Office Action dated Apr. 15, 2008 in co-pending U.S. Appl. No. 10/500,077.
Office Action dated Nov. 28, 2008 in co-pending U.S. Appl. No. 10/500,077.
Final Rejection dated Apr. 14, 2009 in co-pending U.S. Appl. No. 10/500,077.
Notice of Allowance dated Jan. 25, 2010 in co-pending U.S. Appl. No. 10/500,077.
Notice of Allowance dated Apr. 15, 2010 in co-pending U.S. Appl. No. 10/500,077.
Office Action dated Aug. 12, 2010 in co-pending U.S. Appl. No. 10/500,077.
Notice of Allowance dated Dec. 7, 2010 in co-pending U.S. Appl. No. 10/500,077.
Office Action dated Aug. 19, 2009 in co-pending U.S. Appl. No. 11/350,384.
Final Rejection dated May 12, 2010 in co-pending U.S. Appl. No. 11/350,384.
Office Action mailed Aug. 25, 2011 in co-pending U.S. Appl. No. 11/350,384.
Final Rejection mailed Mar. 5, 2012 in co-pending U.S. Appl. No. 11/350,384.
Office Action dated Mar. 16, 2010 in co-pending U.S. Appl. No. 11/584,301.
Office Action Oct. 7, 2010 in co-pending U.S. Appl. No. 11/584,301.
Office Action mailed Dec. 8, 2011 in co-pending U.S. Appl. No. 12/291,814.
International Search Report for PCT/US03/12924, dated Aug. 6, 2003, 2 pages.
International Search Report for PCT/US03/12927 dated Aug. 6, 2003, 3 pages.
International Search Report for PCT/US03/13073 dated Aug. 6, 2003, 7 pages.
International Search Report on PCT/US2008/070482, date of mailing: Apr. 16, 2009, 2 pages.
Written Opinion of the International Searching Authority (Appln. No. PCT/US2008/070482, filed Jul. 18, 2008) mailed Apr. 16, 2009, 4 pages.
International Search Report on PCT/US2011/021341, date of mailing: Sep. 27, 2011, 4 pages.
International Preliminary Examination Report for PCT/US03/12927 dated Feb. 11, 2004, 2 pages.
International Preliminary Examination Report for PCT/US03/12924 dated Jul. 8, 2004, 11 pages.
International Preliminary Report on Patentability (Appln. No. PCT/US2008/070482, filed Jul. 18, 2008) mailed Jan. 27, 2011, pp. 1-6.
International Preliminary Report on Patentability (Appln. No. PCT/US2008/070488, filed Jul. 18, 2008) mailed Jan. 27, 2011, pp. 1-6.
European Search Report, EP 1548420 A3, regarding EP App. No. 04029883, dated Mar. 13, 2006, 4 pages.
European Communication dated Oct. 29, 2010 in a co-pending foreign application (EP10179151.5), 6 pages.
European Communication dated Oct. 29, 2010 in a co-pending foreign application (EP10179183.8), 6 pages.
Indian communication dated Oct. 18, 2010 in a co-pending foreign application (IN1444/DELNP/2004), 2 pages.
Notice of Rejection, with English Translation, dated Jul. 24, 2007 in co-pending Japanese Patent Application No. JP 2003-587467, 6 pages.
Japanese Communication dated Dec. 1, 2010 in a co-pending foreign application JP2008-237495, 3 pages.
Japanese Communication dated Dec. 1, 2010 in a co-pending foreign application JP 2009-111794, 5 pages.
Japanese Communication mailed Dec. 6, 2011 in co-pending Japanese Patent Application No. 2009-282419, 6 pages.
Japanese Communication dated Jul. 27, 2010 in a co-pending foreign application JP2008-070904, 3 pages.
Microbiological Analysis (Sampling Equipment)—Sampling Ports, p. 130, 1989.
Lynx Trademark Reg. No. 2,831,931, first use Apr. 1, 2003, registered Apr. 13, 2003, 3 pages.

Fluid Line Technology Corporation, FLT Bleed/Sample Valve Maintenance, Nov. 10, 2008. Datasheet [online], Fluid Line Technology. Retrieved from the Internet: www.fluidlinetech.com (1 page).
"New quality of data for bioprocessing bags. (Application Area)." Pharmaceutical Processing, Jan. 2002, Charter Medical, Ltd., Bioprocess Products, Retrieved from the Internet on Feb. 16, 2010 from accessmylibrary: <URL: http://www.accessmylibrary.com/coms2/summary_0286-2502274_ITM>, pp. 1-2.
"Rapid Aseptic Fluid Transfer System Introduction" Stedim Biosystems. [online]. Retrieved from the Internet: <URL: http: www.stedim.com/p2A_IDC_introduction.php> (2 pages), dated Nov. 21, 2007.
About Fluid Line Technology, http://www/fluidlinetech.com/aboutus.html dated May 8, 2012 and Oct. 30, 2009, 35 pages.
"Connecting the Sanitary Flange," Datasheet [online], Millipore Corporation, 2007 (pp. 1-2).
Greene, R., et al., "Disposable Equipment: A Mainstay in Bioprocessing", Chemical Engineering Progress, vol. 98, Issue 11, (Nov. 2002), 9 pages.
Guidelines for Using the Lynx ST Connector. Technical Brief [online], Millipore Corporation, 2008. Retrieved from the Internet: www/millipore.com (2 pages).
Haughney, H. and H. Aranha, "Disposable Processing Gains you a Competitive Edge: Enhancing Manufacturing Capacity with Disposable Filters, Connectors, and Membrane Chromatagraphy", Biopharm International, p. 50 (Oct. 2003), 7 pages.
Haughney, H., et al., "Taking Disposable Processing to the Next Level", Clean Rooms, (Jun. 2004), 5 pages.
ESP Sanitary Sample Valves Operation and Maintenance Instructions dated Nov. 1995 (WLG-DEL00039664-WLG-DEL00039678), Millipore Corporation, 16 pages.
Block, S.S. "Disinfection, Sterilization, and Preservation (Fourth Edition)", Lea & Febiger, ISBN:0-8121-1364-0 (1991), 15 pages.
Extended European Search Report mailed Dec. 21, 2010 in co-pending European Patent Application No. 08253748.1.
Casella Sales & Marketing Inc., CSMI Sample Valves. Datasheet [online]. Retrieved from the Internet: www.casellasales.com (2 pages), 2007.
Allegro Single-use Systems—Recommended Capsule Filters and Membranes, http://www.pall.com/main/Biopharmaceuticals/Product.page?id-48022 and http://www.pall.com/variants/print/biopharm_48022.asp, dated May 8, 2012 and Oct. 30, 2009, 51 pages.
Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009, 17 pages.
Daily Business Briefing—"Entegris Introduces the First ALL TEFLON PFA/Process Tee Valve", dated Apr. 16, 2002, 2 pages.
ITT Sample & Bleed Valves. Datasheet [online], ITT Corporation, 2006. Retrieved from the Internet: www.ittpureflo.com (4 pages).
Janetschek, R., "Capsule Filters & Disposable Sterile Processing Systems", Pharmaceutical Processing, vol. 18, No. 11, p. 8 (Jan. 2001), 4 pages.
Landon, R., et al., "Bridging the Gap: A case study in the validation of hybrid connextors", Process PharmaTEC International, issue Jun. 2004, pp. 16-17 (2004).
Lynx ST Connectors http://www.millipore.com/catalogue/module/c9131 dated Oct. 30, 2009, 9 pages.
European Communication mailed Feb. 2, 2010 in co-pending European Patent Application No. 09290917.5, 5 pages
European Communication mailed Jan. 29, 2010 in corresponding European Patent Application No. 09290918.3, 6 pages.
Gore's Fourth Supplemental Response to Millipore's First Set of Interrogatories [Interrogatories Nos. 11 and 12], Civil Action No. 11-346-SLR in the USDC for the District of Delaware, dated May 9, 2012, 172 pages.
Office Action mailed Jun. 26, 2012 in co-pending U.S. Appl. No. 12/872,436.
Final Rejection mailed Jun. 20, 2012 in co-pending U.S. Appl. No. 12/291,814.
English translation of Chinese Communication issued Aug. 29, 2012 in co-pending Chinese patent application No. CN 201010531386.0.

Japanese Communication, with English translation, dispateched Aug. 21, 2012 in co-pending Japanese patent application No. JP 2010-245357.
Office Action mailed Aug. 29, 2012 in co-pending U.S. Appl. No. 12/902,430.
Office Action mailed Oct. 3, 2012 in co-pending U.S. Appl. No. 13/092,566.
Final Rejection mailed Oct. 10, 2012 in co-pending U.S. Appl. No. 12/872,436.
Office Action mailed Oct. 5, 2012 in co-pending U.S. Appl. No. 12/291,814.
Office Action mailed Sep. 30, 2011 in co-pending U.S. Appl. No. 12/638,242.
Japanese Communication, with English translation, mailed Feb. 5, 2013 in co-pending Japanese Patent Application No. JP 2011-179614.
Notice of Allowance mailed Apr. 22, 2013 in co-pending U.S. Appl. No. 11/584,301.
Notice of Allowance mailed Mar. 22, 2013 in co-pending U.S. Appl. No. 13/092,566.
Notice of Allowance mailed Apr. 8, 2013 in co-pending U.S. Appl. No. 12/902,430.
Office Action mailed Nov. 30, 2012 in co-pending U.S. Appl. No. 12/284,666.
Sanitary Inline Bleed and Sample Valves. Datasheet [online], Fluid Line Technology, Retrieved from the Internet: www.fluidlinetech.com (1 page), document created on Mar. 2, 2009 according to document properties.
ITT Dualrange Control Valve. Data Sheet [online], Pure-Flo. Retrieved from the Internet: www.ittpureflo.com (2 pages), document created Jan. 12, 2007 according to document properties.
"Sip-Able Sample Valve," Datasheet [online]. Retrieved from the Internet: www.fluidlinetech.com (1 page), product offered online as early as Jun. 26, 2007, according to URL search performed on http://web.archive.org.
Millipore Publication, NovAseptic, NovaSeptum Liquid Sampling System, dated Nov. 2001, P75185, Rev. B (Bates stamp—WLG-DEL00040809-WLG-DEL00040813), 6 pages.
Entegris Impact Asymmetric Disposable Filters, Product Information brochure, 4414-5723ENT-0511, 2006, 6 pages.
Entegris Impact Mini Disposable Filters, Product Information brochure, 4414-2646ENT-1006, 2006, 4 pages.
Millipore Corporation, Milli-Q Direct Water Purification System brochure, Lit. No. PB1032EN00, Jan. 2012, 8 pages.
Millipore Corporation, Milli-Q Advantage A10 Water Purification Systems brochure, Lit. No. PB0001EN00, 2013, 12 pages.
Japanese Communication, with English translation, mailed Mar. 26, 2013 in co-pending Japanese Patent Application No. 2008-288424.
Office Action mailed May 3, 2013 in co-pending U.S. Appl. No. 12/872,436.
Memorandum and Order Denying Millipore's Motion to Alter Judgment and for Reconsideration, U S District Court for the District of Massachusetts, *EMD Millipore Corporation v. W. L. Gore & Associates, Inc.*, Civil Action No. 09-10765-DPW, Document 83, Dated Mar. 20, 2012, 16 pages.
Gore's Prior Art Statement with Exhibits A through I (entire document), U S District Court for the District of Delaware, *W. L. Gore & Associates, Inc. v. EMD Millipore Corporation*, Civil Action No. 11-346-SLR, Dated Dec. 21, 2011, 55 pages.
Millipore's List of Claim Terms to Be Construed and Proposed Constructions, U S District Court for the District of Delaware, *W. L. Gore & Associates, Inc. v. EMD Millipore Corporation*, Civil Action No. 11-346-SLR, Dated May 30, 2012, 8 pages.
Gore's List of Claim Terms and Proposed Constructions, U S District Court for the District of Delaware, *W. L. Gore & Associates, Inc. v. EMD Millipore Corporation*, Civil Action No. 11-346-SLR, Dated May 30, 2012, 4 pages.
Millipore's Responsive Constructions of Claim Terms, U S District Court for the District of Delaware, *W. L. Gore & Associates, Inc. v. EMD Millipore Corporation*, Civil Action No. 11-346-SLR, Dated Jun. 20, 2012, 5 pages.

Gore's List of Responsive Claim Constructions, U S District Court for the District of Delaware, *W. L. Gore & Associates, Inc. v. EMD Millipore Corporation*, Civil Action No. 11-346-SLR, Dated Jun. 27, 2012, 8 pages.
Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 71, Dated Aug. 8, 2012, 3 pages.
Exhibits 1 and 2 to Gore's Motion for Leave to Amend Its Complaint for Declaratory Judgment, US District Court for The District of Delaware, *W. L. Gore & Associates, Inc. v. EMD Millipore Corporation*, Civil Action No. 11-346-SLR-MPT, Document 75, Redacted-Public Version, Dated Aug. 15, 2012, 241 pages.
Plaintiff Gore's Brief in Support of Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 76, Dated Aug. 15, 2012, Redacted—Public Version, 23 pages.
AESSEAL Environmental Technology P04U and PO5U Single Bellows Component Seal Range, Jan. 2006, (Exhibit 4 to The Affidavit of Alexander H. Slocum, Ph.D., US District Court for the District of Massachusetts, *EMD Millipore Corporation v. AllPure Technologies, Inc.*, Civil Action No. 1:11-cv-10221-DPW,Document 66-4, dated May 2, 2012), 5 pages.
Purdue University-School of Mechanical Engineering-International Compressor Engineering Conference, article by J. W. Abar, "End Face Seals for Air-Conditioning Compressors", 1972 (Exhibit 5 to the Affidiavit of Alexander H. Solcum, Ph.D, US District Court for the District of Massachusetts, *EMD Millipore Corporation v. AllPure Technologies, Inc.*, Civil Action No. 1:11-cv-10221-DPW,Document 66-5, dated May 2, 2012), 15 pages.
Memorandum and Order regarding Claim Construction, U S District Court for the District of Massachusetts, *EMD Millipore Corporation v. Allpure Technologies, Inc.*, Civil Action No. 11-10221-DPW, Document 81, Date Oct. 11, 2012, 34 pages.
Photographs (7 photos) of the Millipore commercially needleless sampling device; available at least as of Feb. 14, 2012, 7 pages.
Photographs (3 photos) of the Millipore Opticap XLT base, commercially available in 2002, no earlier than Jan. 1, 2002, 3 pages.
Photographs (3 photos) of the Millipore Opticap XL 300, commercially available in 2002, no earlier than Jan. 1, 2002, 3 pages.
Brief for Plaintiff-Appellant, US Court of Appeals, Appeal Nos. 2011-1029, 2012-1371, *EMD Millipore Corporation v. W. L Gore & Associates, Inc.*, Document 40, dated Jul. 25, 2012 and filed Jul. 27, 2012 , 147 pages, submitted in 2 parts.
Brief of Defendant-Appellee W. L. Gore & Associates, Inc., US Court of Appeals, Appeal Nos. 2011-1029, 2012-1371, *EMD Millipore Corporation v. W. L Gore & Associates, Inc.*, Document 52, filed Oct. 9, 2012, 75 pages.
Reply Brief for Plaintiff-Appellant, US Court of Appeals, Appeal Nos. 2011-1029, 2012-1371, *EMD Millipore Corporation v. W. L. Gore & Associates, Inc.*, Document 57, Dated Nov. 9, 2012, 42 pages.
AllPure Takeone Aseptic Sampling System Overview, 2 pgs. (Deposition Exhibit dated Nov. 12, 2012).
ASI Life Sciences, three 60, Single Use Aseptic Sampling System, www.asisus.com, Jan. 10, 2013, 8 pages.
Fluid Line Technology Corporation, Product Catalog, 32 pages, Bates No. FLT000003-FLT000034, on information and belief available as of about Nov. 2009.
Gore Single-Use Valve, for Steam-In-Place Applications, 4 pgs. 2009.
Gore STA-PURE Fluid Sampling System, for Single-Use Aseptic Applications, Secure Sampling for Bioprocessing Fluids, Dec. 2008, 4 pages.
Lynx ST Connectors, Millipore Data Sheet, Lit. No. 051750EN00, Rev. E, May 2008, 4 pages.
International Application No. PCT/US03/13073, filed Apr. 25, 2003, and Request for Express Abandonment of U.S. Appl. No. 10/423,131, filed Sep. 11, 2003, 56 pages.
MicropreSure Sanitary Sampling Valves, Millipore Data Sheet, Lit. No. DS1006EN00, May 2005, 4 pages.
Millipore Express SHF Hydrophilic Cartridge Filters, Data Sheet, May 16, 2013, www.millipore.com/catalogue, 2 pages.

Millipore, Hydrophilic Durapore Cartridges and Capsules User Guide, Lit. No. RF 1510EN00, Jan. 2002, 56 pages.

Millipore, Milliflex-P Sanitary Sampling Valves, Operation and Maintenance Instructions, Jul. 2006, 17 pages.

NovaSeptum sampling systems, EMD Millipore Data Sheet, Jun. 2012, Lit. # DS0050EN00, Rev. E., 10 pgs.

NovaSeptum sampling systems, Merck Millipore Data Sheet, Apr. 2013, Lit. # DS0050EN00, Rev. H., 10 pgs.

Millipore, NovaSeptum AV Sterile Sampling System, for liquid sampling, User Guide, Lit. No. 00000069TP, Rev. A., Jun. 2006, 2 pages.

Millipore Opticap XL and XLT Disposable Capsules, Millipore Corporation, Lit. No. PB1700EN00, Rev. B, Jun. 2004, 4 pages.

Pharmaceutical Engineering, vol. 23, No. 3, May/Jun. 2002, pp. 1-8, "Single-Use Disposable Filling for Sterile Pharmaceuticals", Belongia, et al.

Redacted email, dated Jun. 4, 2012, regarding Disposable Steam Connector, 2 pages.

Millipore, Series 2000, Single Sanitary Cartridge Housing, Instructions for Installation and Maintenance, Lit. No. P35265, Rev. A, Feb., 2000, 12 pages.

ThermoScientific, Data Sheet 053, Rev. 2, "Aseptic Connection Devices", 2008, 2 pages.

Final Rejection mailed Jun. 19, 2013 in co-pending U.S. Appl. No. 12/291,814.

Notice of Allowance mailed Jun. 21, 2013 in co-pending U.S. Appl. No. 12/284,666.

Notice of Allowance mailed Jul. 8, 2013, in co-pending U.S. Appl. No. 12/284,666.

Notice of Allowance mailed Jul. 3, 2013 in co-pending U.S. Appl. No. 13/092,566.

Notice of Allowance mailed Jul. 5, 2013 in co-pending U.S. Appl. No. 11/584,301.

* cited by examiner

DEVICE FOR THE TRANSFER OF A MEDIUM

FIELD OF THE INVENTION

The present invention concerns the transfer of media, such as liquids, into or from a container.

BACKGROUND OF THE INVENTION

It is especially important, in particular in the field of pharmaceutics and biotechnologies, to be able to take off samples to analyze them, for example to perform microbiological verifications in culture tanks, for counting cells, for chemical analysis, etc.

Such taking off must be performed while minimizing as much as possible the risks of contamination of the taken-off sample and of the medium from which the sample is taken off.

A device is already known, in particular from the United States patent U.S. Pat. No. 7,293,477, for the transfer of a medium into or from a container comprising a magazine having two main faces of which one is adapted to cooperate with the container and a lateral face extending between the main faces as well as several sliding valves housed in cavities of the magazine. In each valve there is formed a duct for transfer of the medium which issues at the face cooperating with the container, each valve having a closed position in which it sealingly isolates that duct from the container and an open position in which that duct is placed in communication with the container.

Each duct also communicates via an end-piece and a flexible tube with a bag for transferring the medium from the container to the bag.

To make each valve pass from its closed position to its open position, the operator presses on a tab of that valve to unlock it from the magazine and make it slide along a portion made of elastomer of that magazine in order for it to occupy its open position. In this position, the end portion of the valve projects within the container, so placing the duct of that valve in communication with the container. To pass the valve back to its closed position, the operator pulls on it to make it slide in the opposite direction.

SUMMARY OF THE INVENTION

The invention aims to provide a device that is also adapted to enable the transfer of a medium, but more economically, more practically, and with better performance.

To that end it provides a device for the transfer of a medium into or from a container comprising a magazine having two main faces of which one is adapted to cooperate with said container and a lateral face extending between said main faces as well as at least one sliding valve housed in a cavity of said magazine and in which there is formed a transfer duct for said medium which issues on said face adapted to cooperate with said container, said valve having a closed position in which it sealingly isolates said duct from said container and an open position in which said duct is placed in communication with said container; characterized in that said valve comprises a valve member, an isolation sleeve surrounding at least partially said valve member as well as spring means adapted to be compressed by said valve member when said valve is in its open position.

In the device according to the invention, the sleeve (providing sealing with the magazine) and valve member (opening or closing the valve) arrangement makes it possible in particular to obtain better sealing than in the device of the prior art.

This is because in the device of the prior art the sealing with the magazine is provided by a part moving in sliding translation (the body of the sliding valve) whereas in the device according to the invention these two functions are dissociated, the only function of the valve member being to open or close the valve whereas sealing with the magazine is provided by the non-moving isolation sleeve which ensures sealing of better quality (less risk of leakages between the valve and the magazine) since the surfaces of the sleeve are in non-sliding contact with the magazine.

Furthermore, the fact that spring means are provided for the valve with those spring means being compressed when the valve is open enables the valve to be held in its closed position until it is actuated and to dispense with the locking means of the prior art device which enables the dimensions of such a device to be minimized and to free considerable space in which to place, in a magazine of the same diameter as that of the prior art device, more valves (so increasing the number points for take-off from the container).

Lastly, the presence of spring means enables automatic return of the valve to its closed position without additional manipulation once the transfer has been carried out which not only makes such a device more sure but also gives it better performance.

It is to be noted that still other types of transfer devices exist comprising a magazine, such as the device described in European patent EP 0 858 589, such devices having a needle intended for perforating a septum. The device according to the invention enables such needles to be dispensed with and thus also makes that device simpler, more ergonomic and cheaper.

According to features that are preferred for reasons of simplicity and convenience for both manufacture and use, said duct also issues on said lateral face.

The issuing of the transfer duct on the lateral surface of the magazine, that is to say radially relative to the direction of sliding of the valve member in the sleeve, makes it possible to leave free the opposite face of the magazine to that which cooperates with the container to thereby have easy access to the valve member in order to be able to actuate it and make the valve pass from its closed position to its open position.

The exploitation of the lateral surface of the magazine to form the outlet from the duct also contributes to making such a device more compact by optimizing the set of available useful surfaces.

According to still other preferred features, said cavity is open at the opposite main face to that adapted to cooperate with said container.

This opening thus directly gives access to the valve member so making its actuation simple and easy.

According to still other preferred features, said sleeve comprises at least one elastically deformable portion forming said spring means.

By fulfilling the spring function, the elastically deformable portion of the sleeve makes it possible to greatly simplify the manufacture and reliability of such a device since it is not necessary to add another component to the valve to provide the elastic return of the valve member to the closed position.

According to still other preferred features:

in said closed position of the valve, a space is present between said magazine and said elastically deformable portion of said sleeve, said space being at least partially occupied by that portion in its compressed state when the valve is in its open position.

said valve member has a head in sealing contact with said sleeve in the closed position and away from said sleeve in the open position, a shank and a body linked to the opposite end of the shank to that linked to the head; and/or the body of said valve member is in abutment with said spring means in said open position and, on the opposite end to said surface in abutment with said spring means, has an actuating surface for passing said valve from its closed position to its open position.

According to still other preferred features, said shank has a portion in sealing contact with said sleeve and a portion without contact with said sleeve.

The presence of a valve member portion in contact with the sleeve and a portion without contact makes it possible not only to provide sealing between the valve member and the sleeve but also to leave a space between that valve member and that sleeve to form a part of the transfer duct for the medium.

According to still other preferred features:

the device also comprises means for actuating said valve to make it pass from its closed position to its open position;

said actuating means are adapted to hold said valve in its open position;

said actuating means are rotatably mounted on said magazine;

said actuating means comprise a manipulating wheel provided with a nipple for actuating said valve, said nipple has a curved surface and a flat surface.

said magazine has indexing means and said manipulating wheel has complementary indexing means adapted to index said manipulating wheel relative to said magazine in a position in which said nipple presses against said valve member and in a position in which it is away from said valve member;

said actuating means comprise a projection movable in a track formed in a wall of said magazine, a rotatably mounted ring on said magazine adapted to drive the movement of said projection in said track to place it facing said valve member to actuate, as well as a button adapted to actuate said valve member via said projection; and/or said magazine comprises several cavities in each of which is accommodated a corresponding valve, said cavities being disposed around the center of said magazine.

BRIEF DESCRIPTION OF THE DRAWINGS

The features and advantages of the invention will appear from the following description, given by way of preferred and non-limiting example, with reference to the accompanying drawings in which.

DETAILED DESCRIPTION OF THE INVENTION

Figure 1:
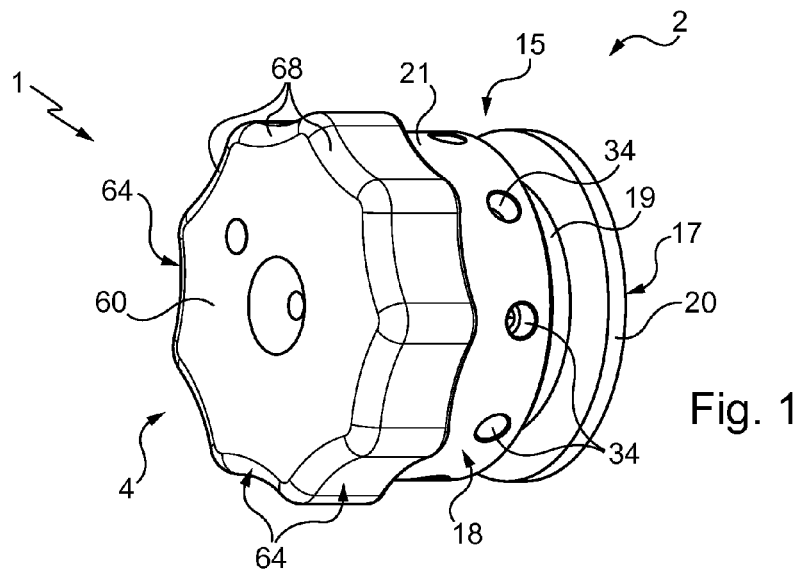
FIGS. 1 and 2 are two perspective views taken from different angles of a device according to the invention and on which the nine valves which it comprises are represented in their closed position.
Figure 2:
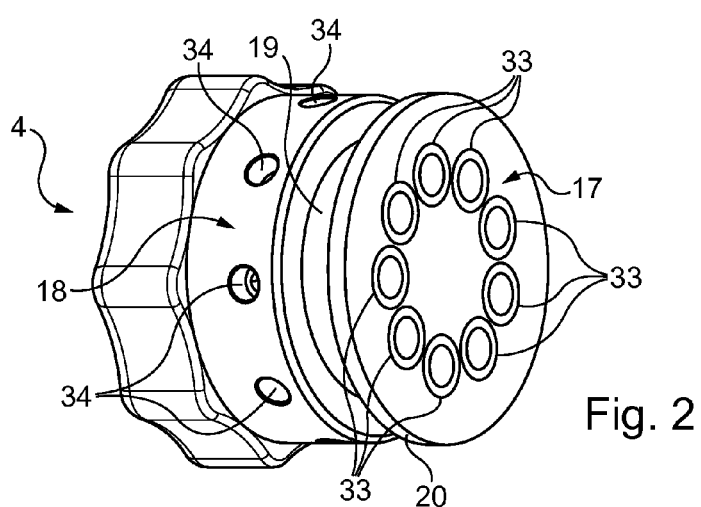
Figure 3:
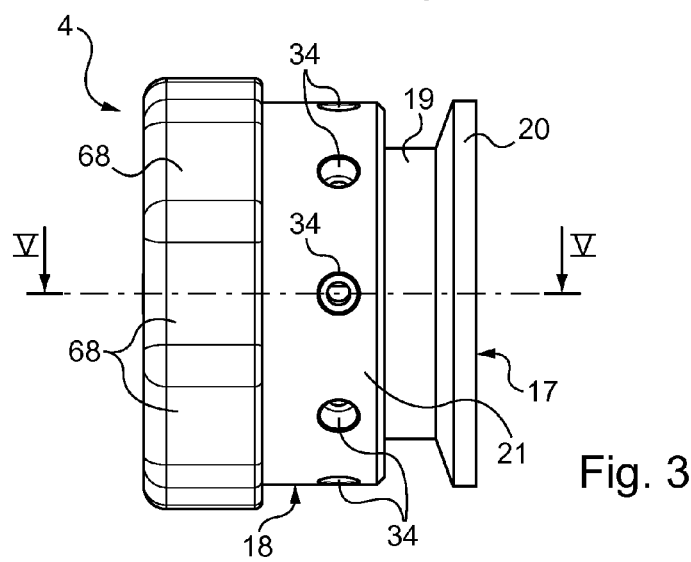
FIG. 3 is a view in elevation of that device.
Figure 4:
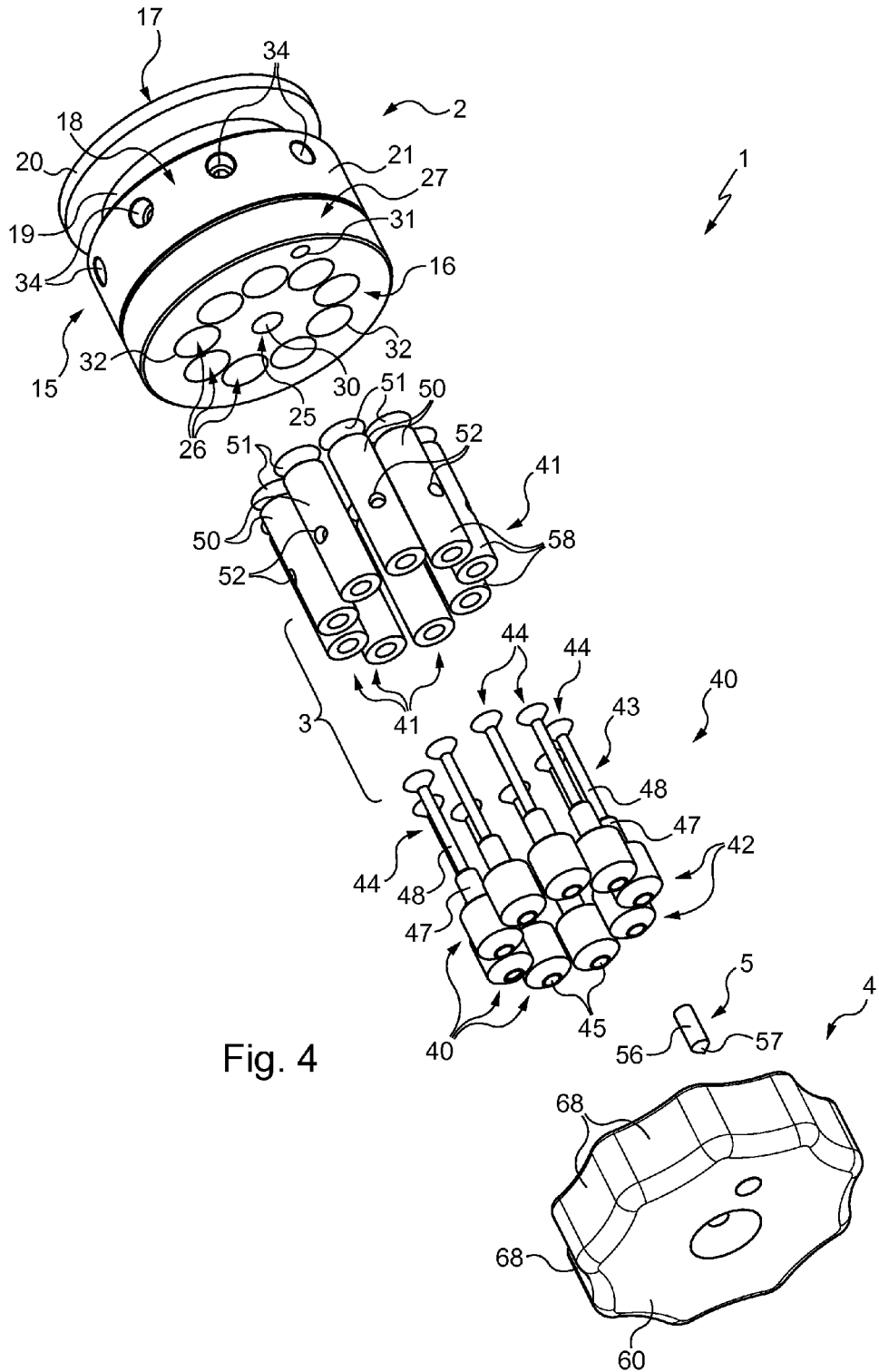
FIG. 4 is an exploded view in perspective of that device.

The transfer device 1 illustrated in FIGS. 1 to 6 comprises a magazine 2, nine valves 3, an actuating manipulating wheel 4 as well as an indexing finger 5 (FIG. 4).

Figure 10:
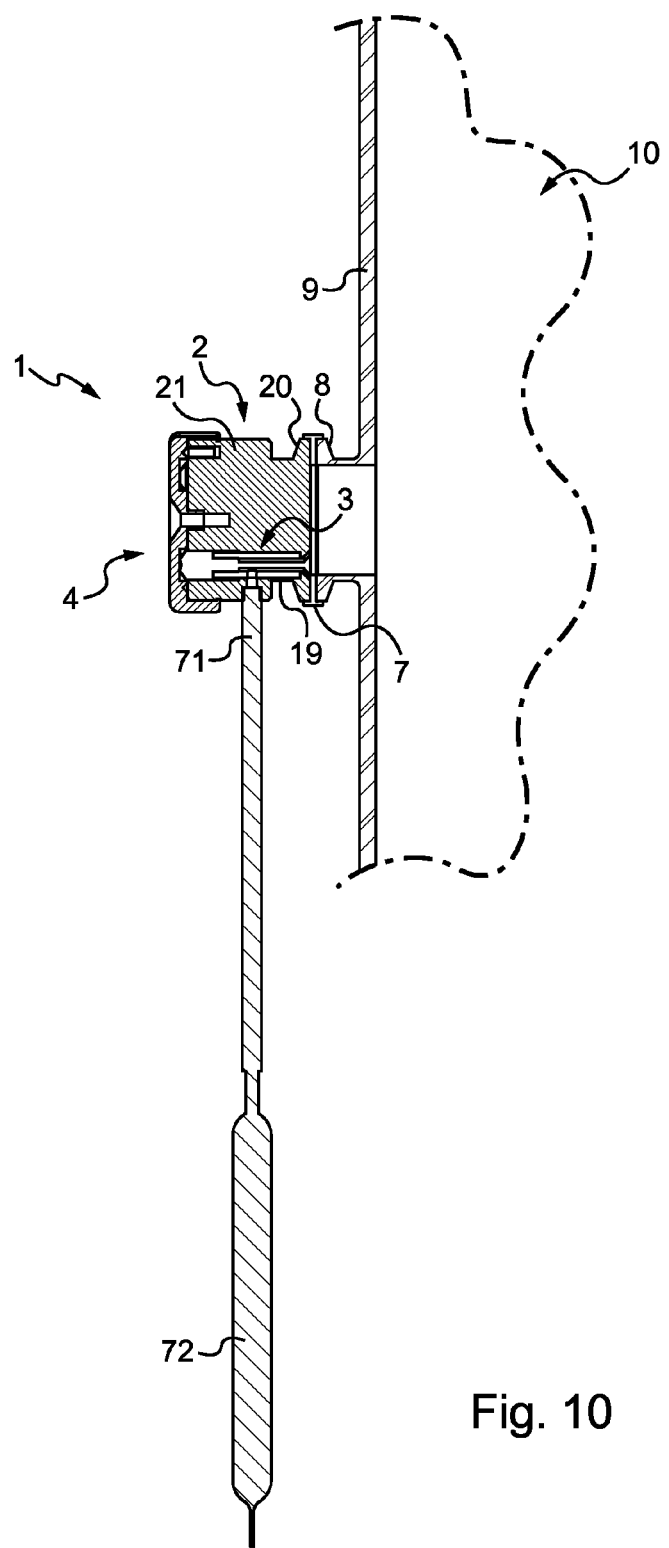
FIG. 10 is a cross-section view in elevation of that device fixed to the wall of a container to which a take-off bag is connected.

As illustrated in FIG. 10, this device 1 is to be assembled (for example by screwing or latching) via a seal 7 to a coupling 8 which is formed on the wall 9 of a container 10 and in which an opening (not visible) is formed to enable each of the nine valves of the magazine to be place in communication with the inside of the container.

Each valve is also associated with a bag 72 provided to receive the medium coming from the container (for example a liquid), each bag being connected the magazine 2 by a tube 71.

The magazine 2 of the transfer curve comprises a body 15 having two main faces 16 and 17 (FIG. 4) and a lateral face 18 linking said main faces together.

The body 15 is of plastics material and has a general form that is cylindrical with the exception of a recess 19 separating on one side a collar 20 which delimits the face 17 and which is adapted to cooperate with the coupling 8 of the container and a cylindrical portion 21 adapted to cooperate with the manipulating wheel 4.

In the body there are formed a central cavity 25, nine lateral cavities 26 disposed side by side in a circle, concentrically about the cavity 25 and approximately half way between the center of the magazine and its periphery, as well as a cavity 27 situated at the edge of that body.

Cavity 25 (and respectively 27) only issues at face 16, by an opening 30 (and respectively 31).

Each cavity 26 issues from face 16 by an opening 32, from face 17 by an opening 33 (FIG. 2) and from the lateral face by an opening 34.

Figure 5:
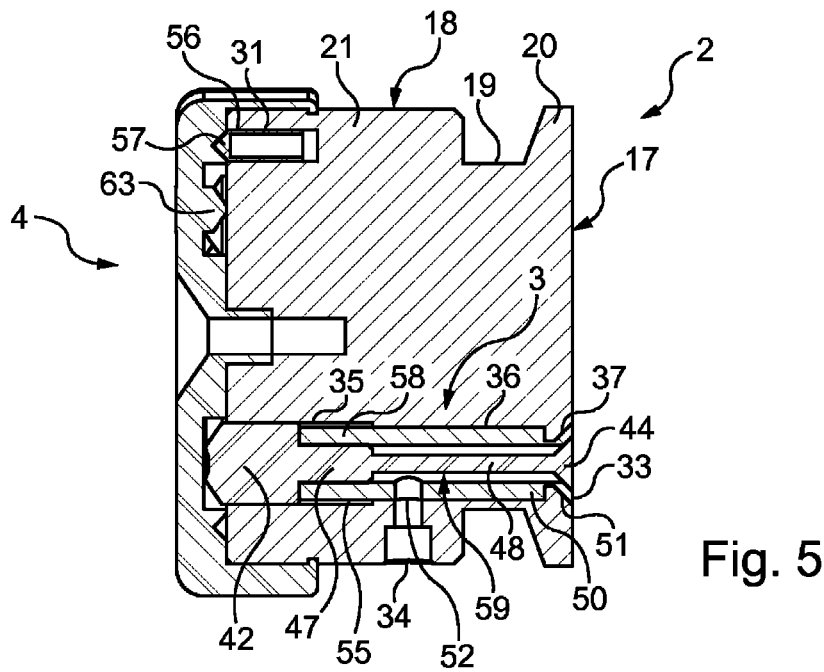
FIG. 5 is a cross-section view in elevation of that device taken on line V-V of FIG. 3 in which the valve which is in cross-section is represented in its closed position.
Figure 6:
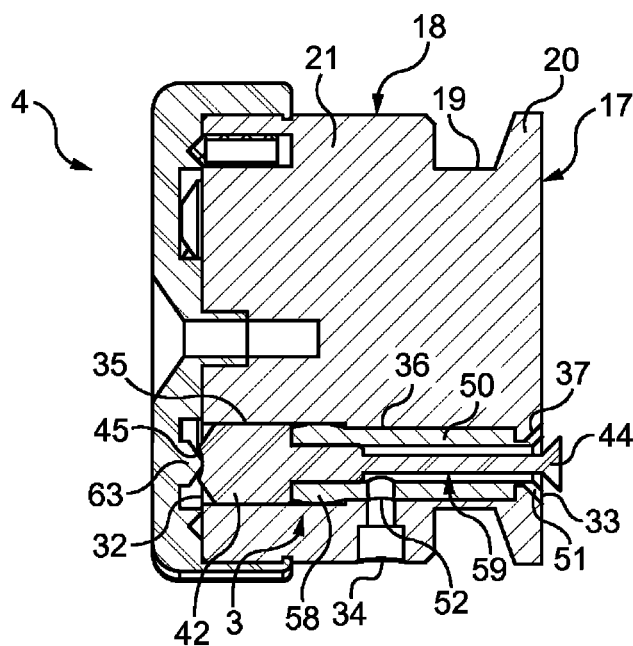
FIG. 6 is a similar view to FIG. 5, but in which that valve is represented in its open position.

As illustrated in FIGS. 5 and 6, each cavity 26 is delimited by a first hollow portion 35, a second hollow portion 36 of smaller inside diameter than the inside diameter of the first portion 35 and a hollow portion 37 extending in the direction of face 17 and flaring as it does so.

Each valve comprises a valve member 40 and a sealing sleeve 41.

The valve member is of thermoplastics material and the sleeve is formed from an elastomer material, that is to say that it is elastically deformable and enables sealing to be provided both with the valve member 40 and with the magazine 2.

The valve member 40 comprises a body 42, a shank 43 and a head 44.

The body 42 is a solid bar of outside diameter substantially equal to the inside diameter of portion 35 of the cavity and, at its top, at the opposite end from the head 44, comprises a bowl-shaped recess 45 adapted to receive, as will be seen below, an actuating nipple comprised by the manipulating wheel.

Shank 43 comprises a first cylindrical portion 47, a second cylindrical portion 48 of smaller diameter than the diameter of portion 47 and attached to that first portion at the opposite end to the body 42.

Lastly, the head is in the form of a frusto-conical collar and connects to the cylindrical portion 48 at the opposite end to portion 47.

The sleeve 41 comprises a first tubular portion 50 and a flared portion 51 respectively espousing the inside surface of the hollow portion 36 of the magazine and that of the flared portion 37.

The tubular portion 50 of the sleeve comprises an opening 52 provided approximately half way between its edges.

This sleeve is engaged in the corresponding cavity 26 of the magazine with the conical portion 51 coming into abutment against the conical portion 37 of the magazine and the tubular portion 50 accommodating in the hollow portion 36 of the cavity with a part 58 of that tubular portion projecting from that cavity inside the hollow portion 35, such that there is play 55 between that portion 58 and the portion 35 of the magazine (FIG. 5), that play, as will be seen below, enabling the dilation of that portion of the sleeve 41 when the sleeve is compressed.

Once the sleeve has been engaged, the opening 52 of that sleeve is situated facing the corresponding opening 34 of the magazine (FIGS. 5 and 6).

In addition to sealing with the head 44 of the valve member, the sleeve 41 also provides sealing with the tubular portion 47 of that valve member as well as the sealing with portion 36 of the magazine 2.

The valve member 40 accommodates in the sleeve with the body 42 being disposed against the edge of part 58 of the tubular portion 50. Portion 47 of the shank 43 is in sealing contact with portion 50 at its part 58 whereas portion 48 is away from portion 50 within the latter, such that it delimits a space with that portion 50 enabling the passage of the medium to transfer.

Cavity 26, valve member 40 and sleeve 41 thus delimit a duct 59 (FIGS. 5 and 6) extending from the opening 33 to the opening 34 of the magazine 2 and comprising the space situated between the sleeve 41 and the portion 48 of the valve member as well as the space situated between the opening 52 of the sleeve and the opening 34 of the magazine.

In the closed position of each valve 3 illustrated in FIG. 5, the head 44 comes to bear against the flared portion 51 of the sleeve 50 itself bearing against the magazine so as to provide the sealed isolation of the duct 59 with the container.

In this position, the surface of the head 44 turned towards the container is situated at the same level as the surface 17 of the magazine (which in particular makes it possible not to have any obstacle in the vicinity of the opening 33 and thus no risk of having liquid stagnating in the vicinity of that opening, the taking-off from the container then risking not being representative).

In the open position of the valve 3 illustrated in FIG. 6, the head 44 of the valve member is away from the flared portion 51 of the sleeve and projects within the container, so enabling the medium to be transferred to enter the duct 59 by the opening 33 between the head 44 of the valve member and the portion 51 of the sleeve to exit that duct by the opening 34.

The finger 5 illustrated in FIG. 4 comprises a cylindrical portion 56 and a conical portion 57 and accommodates in the cavity 27 of the magazine, a spring being disposed at the innermost end of that cavity (not shown on the drawings).

Figure 7:
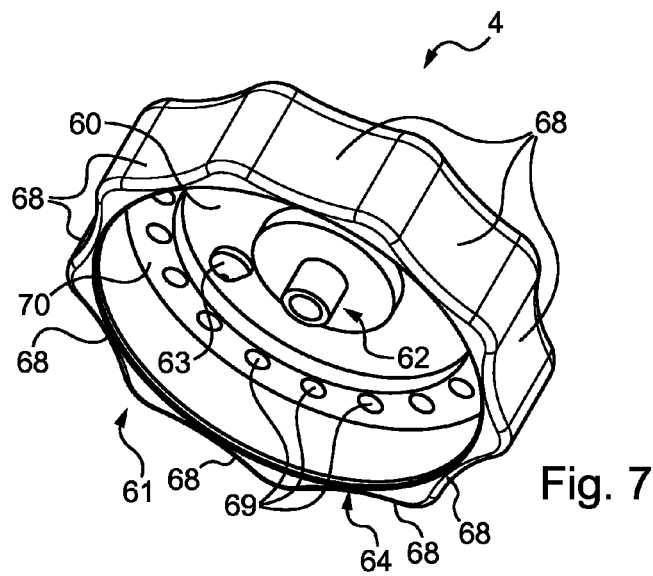
FIGS. 7 to 9 are respectively a view in perspective, a plan view taken from below and a cross-section view in elevation on line IX-IX of FIG. 8 illustrating an actuating manipulating wheel that this device comprises.
Figure 8:
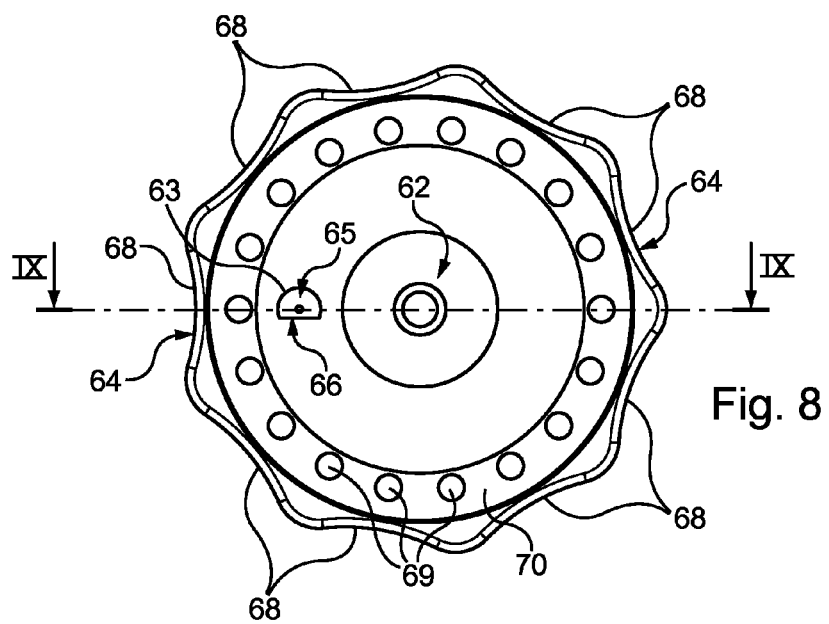
Figure 9:
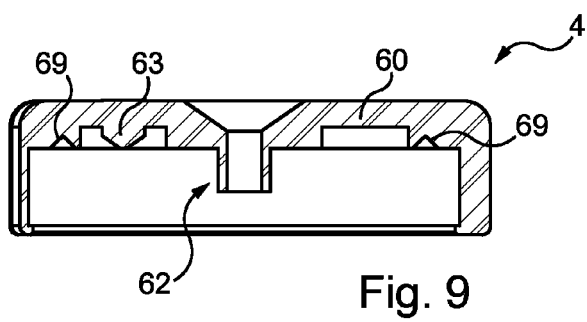

The manipulating wheel 4 is described next with reference to FIGS. 7 to 9.

This manipulating wheel 4 comprises a back 60 and a collar 61 radially surrounding that wall, a journal 62 and actuating nipple 63.

This manipulating wheel also comprises an annular rib 70, projecting from the back wall on the same side as the collar 61, in which there are formed eighteen regularly spaced blind indexing holes 69.

The collar 61 comprises nine wall segments 68 linked together and each comprising an outwardly directed concave face 64 facilitating the grasping of that manipulating wheel by the fingers of the operator.

The nipple 63 has a curved surface 65 and a flat surface 66.

The manipulating wheel 4 is disposed against the face 16 of the magazine 2 with the journal 62 being engaged in the central accommodation 25 of that magazine such that the manipulating wheel is mounted to rotate on that magazine.

The eighteen blind holes are each provided to receive the cone 57 of the finger 5, those eighteen holes thus corresponding to the same number of relative indexing positions of the manipulating wheel relative to the magazine.

In nine of those indexing positions, the nipple 63 bears against a valve member 42, such that the corresponding valve is open. In the other nine positions, termed waiting positions, the nipple 63 is situated between two valve members 42 such that all the valves are closed, those positions alternating with the nine positions in which one of the valves is open.

Rotating the manipulating wheel thus makes it possible to alternate the positions in which the valves are open one after the other and the positions in which all of those valves are closed, so isolating all the ducts 59 of the magazine from the inside of the container.

Due to its simplicity, the device 1 is obtained by simple molding of all the members that constitute it, it thus being possible for the device to be a single-use (disposable) device for reasonable cost.

This device can withstand strong operating pressure of the order of one bar or even more.

A description will now be given of how to perform a take-off operation from a medium, such as liquid, inside a container, in particular with reference to FIGS. 5, 6 and 10.

Prior to the taking-off operations, the device 1 is sealingly fixed to the coupling of the container as illustrated in FIG. 10, with the finger 5 being indexed in a hole 69 corresponding to one of the nine positions in which all the valves are closed.

To perform a take-off operation into one of the bags 72 (FIG. 10), the operator acts on the manipulating wheel and turns it clockwise. During this rotation, the rib 70 exerts a force on the cone 57 of the indexing finger such that the finger is thrust into its cavity 27 so concealing the hole 69 in which it was housed to enable the manipulating wheel to turn.

The operator continues to turn the manipulating wheel 4 until the indexing finger 5 comes to be accommodated in the neighboring blind hole 69 by elastic return of the spring (not shown).

During the movement, the curved surface 65 of the nipple 63 encounters the body 42 of one of the valve members and comes to press thereon for it to slide until the nipple is accommodated in the recess 45 of the body 42 (FIG. 6).

The curved surface 65 of the nipple and that of the head 42 facilitate the engagement of that nipple in the recess 45.

In this position the first of the nine valves 3 is then open so enabling the liquid to flow through the duct 59 of that valve then through the tube 71 connected to the opening 34 of that duct 59 until it reaches the bag 72 (FIG. 10).

In this position, the body 42 of the valve member is in abutment and bears against the edge of part 58 of the sleeve 41 such that this part of the sleeve is compressed and has a slightly convex shape thereby occupying a large part of the space 55 which was left free between it and the magazine adjacent portion 55 when that sleeve was at rest (not compressed).

When the operator passes to the following position and thus separates the nipple 63 from that valve member, this compression enables the natural return of the valve member to its initial position (closed position) by elastic return of that part 58 of the sleeve.

Once the bag 72 attached to that valve is sufficiently filled, the operator thus again turns the manipulating wheel 4 in the same direction as earlier until the cone 57 of the finger 5 is disposed in the next blind hole 69, corresponding to one of the nine positions in which the nipple 63 is disposed between two valve members, all the valves then being in their closed position, which makes it possible to wait before performing the next take-off operation without any valve remaining open.

With the device illustrated here it is thus possible to perform nine take-off operations successively with, between each take-off operation, a position in which all the valves are closed.

After the filling of each bag, it is possible to retrieve that bag using a tool (not illustrated) adapted to cut out all while obturating the tube 71 (for example by heating).

If, when the manipulating wheel is indexed to a waiting position, the operator were to act on the manipulating wheel in the opposite direction, the flat surface 66 of the nipple 63 would come into abutment against the body 42 of the valve member to prevent the manipulating wheel from turning further, such that it is made impossible to open a valve again that had already been opened previously, this being to avoid any risk of having the different samples of liquid taken off contaminated by each other.

Nothing however prevents the return from a position in which a valve is open to the preceding waiting position since the nipple 63 does not come into abutment against a valve member in that case, which thus makes it possible to perform several successive take-off operations by the same valve and to close that valve between each take-off operation.

An end of travel abutment rib (not illustrated in the drawings) is also present to prevent turning the manipulating wheel further once all the valves have been opened, so as not to open the first of those valves again by turning the manipulating wheel in the same direction as previously.

Figure 11:
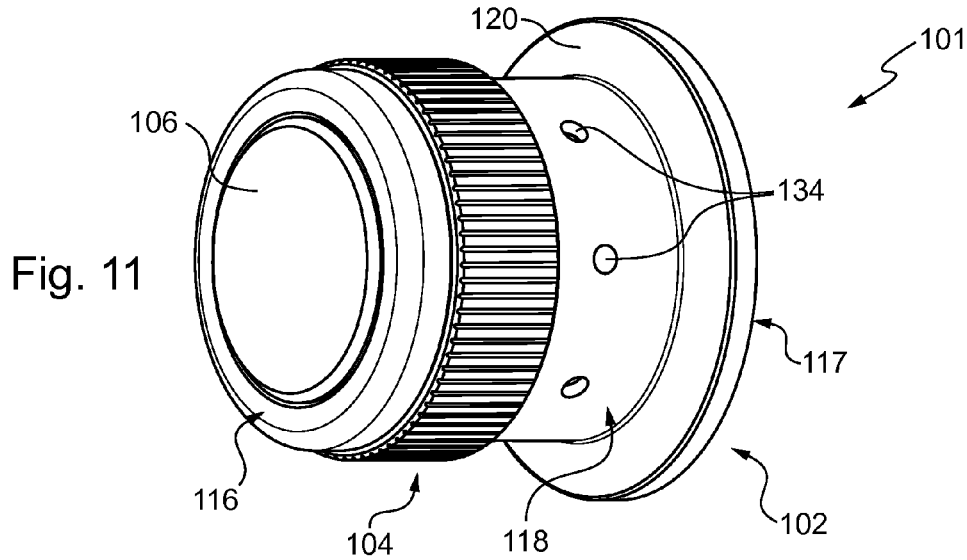
FIG. 11 is a perspective view of second embodiment of the device according to the invention.
Figure 12:
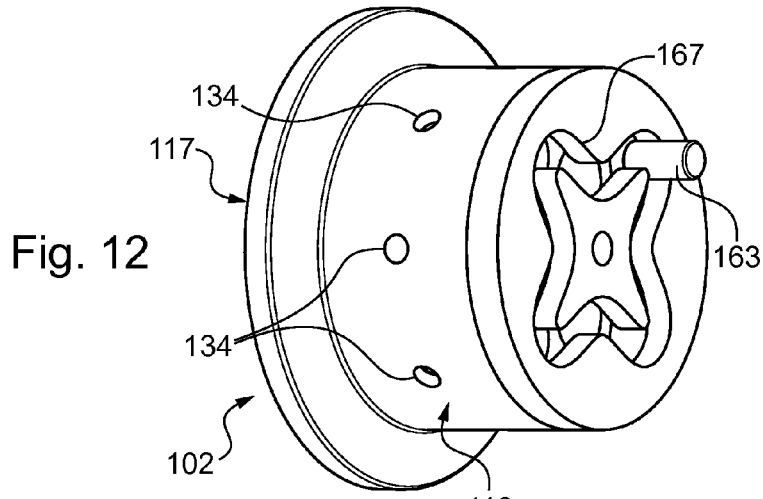
FIG. 12 is a similar view to FIG. 11, but for which some parts of the device have not been shown.
Figure 13:
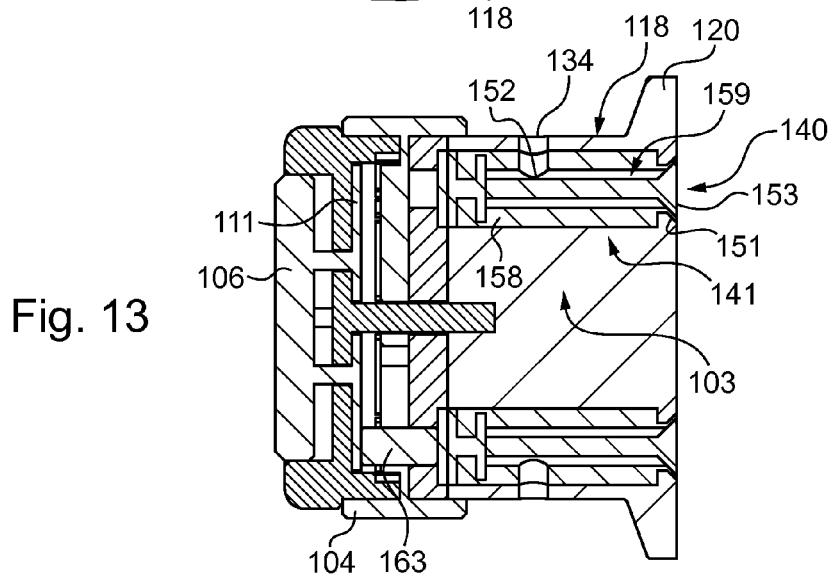
FIG. 13 is an elevation view of that device in cross-section along a median plane of symmetry.

Another embodiment of the transfer device is illustrated in FIGS. 11 to 13.

Generally, for similar members the same references have been used, to which the number 100 has been added.

The transfer device 101 comprises a magazine 102, a ring 104 and an actuating button 106.

This device also comprises a moveable projection 163 within a track of closed outline 167 delimited by the upper portion of the magazine 102 (FIG. 12). This moveable projection 163 cooperates with the ring 104 such that, when the operator causes that ring to turn, the ring acts directly on the projection 163 and causes it to move within the track in order for that projection to be disposed facing one of the valve members 140 to actuate.

That ring 104 also comprises indexing means (not visible) and the magazine comprises complementary indexing means (also not visible) to index the projection 163 when facing each valve member 140.

When the projection 163 faces the desired valve member, the operator presses on the push button 106 in order to bear on the projection 163 via a plate 111 in order for that projection to cause the corresponding valve member to slide towards face 117 and to compress the sleeve 141 while at the same time separating the head of that valve member from its sleeve so as to place the inside of the duct 159 of that valve in communication with the enclosed space from which it is desired to take off a sample.

In another embodiment not illustrated, each valve 3 of the device is connected by a flexible tube not to a single bag but to several bags arranged in series, those bags filling successively during the transfer of the liquid until that liquid occupies the last bag which serves as a filling indicator indicating to the operator that all the preceding bags have been filled and that he may close the valve.

In another embodiment not illustrated, the spring-forming portion 58 of the sleeve is replaced by any other type of spring means such as a spiral spring, the valve member possibly being surrounded by an 'O' ring to isolate the spring from the medium to transfer.

In still another embodiment not illustrated, the device has more or fewer than nine take-off points by varying the diameter of the magazine or not.

In still another embodiment not illustrated, the device lacks actuating means such as a manipulating wheel and the access to the valve member is left free at face 16 to enable the operator to act directly thereon.

Such devices are usable for other media than liquid media, such as a gas to take off for analysis or for any other type of fluid medium.

It is also to be noted that the device according to the invention makes it possible to perform the transfer of a medium not necessarily from the container to the bags but also, for example, from a bag pre-filled with medium to a container.

The device according to the invention is also intended for transferring a medium into or from any type of container other than a tank, such as containers with flexible walls such as a bag or a pipe, a connector being mounted on those containers adapted to cooperate with a magazine.

The present invention is not limited to the embodiments described and represented but encompasses any variant form thereof.

The invention claimed is:

1. A device for the transfer of a medium into or from a container, comprising:
    a magazine having two main faces of which one is adapted to cooperate with the container, the magazine comprising at least one cavity extending between the two main faces and a lateral face extending between the two main faces, the lateral face having an opening;
    at least one sliding valve housed in the at least one cavity of the magazine, the sliding valve and the cavity forming a transfer duct for the medium, the transfer duct extending from an opening in the face adapted to cooperate with the container to the opening in the lateral face, the sliding valve having a closed position to sealingly isolate the transfer duct from the container and an open position to place the transfer duct in communication with the container, the sliding valve comprising:
        a valve member, and
        an isolation sleeve surrounding at least partially the valve member, the sleeve comprising at least one elastically deformable portion adapted to be compressed by the valve member when the sliding valve is in the open position; and
    an actuating member configured to displace the valve member with rotation of the actuating member to pass the sliding valve from the closed position to the open position.

2. The device of claim 1, wherein the valve member is displaced linearly.

3. The device of claim 1, wherein the valve member is displaced toward the container.

4. The device of claim 1, wherein the cavity is open at the main face opposite to the face that is adapted to cooperate with the container.

5. The device of claim 1, wherein, in the closed position of the valve, a space is present between the magazine and the elastically deformable portion of the sleeve, the space being at least partially occupied by the elastically deformable portion when the elastically deformable portion is compressed by the valve member when the valve is in the open position.

6. The device of claim 1, wherein the valve member comprises a head in sealing contact with the sleeve in the closed position and spaced apart from the sleeve in the open position, the valve member further comprising a shank and a body, the body linked to an end of the shank and the head linked to an opposite end of the shank.

7. The device of claim 6, wherein the body of the valve member has a surface in abutment with the elastically deformable portion when the valve is in the open position and, on the end opposite to the surface in abutment with the elastically deformable portion, has an actuating surface to pass the valve from the closed position to the open position.

8. The device of claim 6, wherein the shank has a portion in sealing contact with the sleeve and a portion without contact with the sleeve.

9. The device of claim 1, wherein the actuating member is adapted to hold the valve in the open position.

10. The device of claim 1, wherein the actuating member is rotatably mounted on the magazine.

11. The device of claim 1, wherein the actuating member comprises a manipulating wheel provided with a nipple for displacing the valve member.

12. The device of claim 11, wherein the nipple has a curved surface and a flat surface.

13. The device of claim 11, wherein the magazine has an indexing structure and the manipulating wheel has a complementary indexing structure adapted to index the manipulating wheel relative to the magazine in a position in which the nipple presses against the valve member and in a position in which the nipple is spaced apart from the valve member.

14. The device of claim 1, wherein the magazine comprises plural cavities being disposed around the center of the magazine, each cavity configured to accommodate a corresponding valve.

15. A device for the transfer of a medium into or from a container, comprising:
a magazine having two main faces of which one is adapted to cooperate with the container, the magazine comprising at least one cavity extending between the two main faces and a lateral face extending between the two main faces, the lateral face having an opening;
at least one sliding valve housed in the at least one cavity of the magazine, the sliding valve and the cavity forming a transfer duct for the medium, the transfer duct extending from an opening in the face adapted to cooperate with the container to the opening in the lateral face, the sliding valve having a closed position in which it sealingly isolates the transfer duct from the container and an open position in which the transfer duct is placed in communication with the container, the sliding valve comprising:
a valve member, and
an isolation sleeve surrounding at least partially the valve member, the sleeve comprising at least one elastically deformable portion adapted to be compressed by the valve member when the sliding valve is in the open position; and
an actuating member configured to linearly displace the valve member to pass the sliding valve to the open position, the elastically deformable portion being configured to provide elastic return of the valve member to pass the sliding valve to the closed position.

16. The device of claim 15, wherein the valve member comprises a head in sealing contact with the sleeve in the closed position and spaced apart from the sleeve in the open position, the valve member further comprising a shank and a body, the body linked to an end of the shank and the head linked to an opposite end of the shank.

17. The device of claim 16, wherein the body of the valve member has a surface in abutment with the elastically deformable portion when the valve is in the open position and, on the end opposite to the surface in abutment with the elastically deformable portion, has an actuating surface to pass the valve from the closed position to the open position.

18. The device of claim 15, wherein the actuating member is rotatably mounted on the magazine.

19. The device of claim 15, wherein the actuating member comprises a manipulating wheel provided with a nipple for displacing the valve member.

20. The device of claim 19, wherein the magazine has an indexing structure and the manipulating wheel has a complementary indexing structure adapted to index the manipulating wheel relative to the magazine in a position in which the nipple presses against the valve member and in a position in which the nipple is spaced apart from the valve member.

21. The device of claim 15, wherein the actuating member comprises a projection movable in a track formed in a wall of the magazine, a rotatably mounted ring on the magazine adapted to drive the movement of the projection in the track to place the projection in a position facing the valve member, and a button adapted to displace the valve member via the projection.

22. The device of claim 15, wherein the magazine comprises plural cavities being disposed around the center of the magazine, each cavity configured to accommodate a corresponding valve.

23. A device for the transfer of a medium into or from a container, comprising:
a magazine having two main faces of which one is adapted to cooperate with the container, the magazine further comprising plural cavities extending between the two main faces and a lateral face extending between the two main faces, the lateral face having plural openings, each opening corresponding to one of the cavities;
a plurality of sliding valves, each sliding valve housed in one of the cavities of the magazine, each sliding valve and respective cavity forming a transfer duct for the medium, the transfer duct extending from an opening in the face adapted to cooperate with the container to that opening in the lateral face corresponding to the cavity, each sliding valve having a closed position to sealingly isolate the transfer duct from the container and an open position to place the transfer duct in communication with the container, each sliding valve comprising:
a valve member, and
an isolation sleeve surrounding at least partially the valve member, the sleeve comprising at least one elastically deformable portion adapted to be compressed by the valve member when the sliding valve is in the open position, the valve member comprising a head in sealing contact with the sleeve in the closed position; and an actuating member configured to successively pass each of the sliding valves from the closed position to the open position.

24. The device of claim 23, wherein the actuating member is configured to linearly displace the valve member of each valve to pass the valve to the open position, the elastically deformable portion being configured to provide elastic return of the valve member to pass the valve to the closed position.

25. The device of claim 23, wherein the actuating member comprises a manipulating wheel provided with a nipple for displacing each valve member.

26. The device of claim 25, wherein the magazine has an indexing structure and the manipulating wheel has a complementary indexing structure adapted to index the manipulating wheel relative to the magazine in a position in which the nipple presses against each valve member and in a position in which the nipple is spaced apart from the valve member.

27. The device of claim 23, wherein the actuating member comprises a projection movable in a track formed in a wall of the magazine, a rotatably mounted ring on the magazine adapted to drive the movement of the projection in the track to place the projection facing the valve member of one of the valves, and a button adapted to displace the valve member via the projection.

28. The device of claim 23, wherein the cavities are disposed around the center of the magazine.

* * * * *

UNITED STATES PATENT AND TRADEMARK OFFICE
CERTIFICATE OF CORRECTION

| | | |
|---|---|---|
| PATENT NO. | : 8,539,988 B2 | Page 1 of 1 |
| APPLICATION NO. | : 12/638283 | |
| DATED | : September 24, 2013 | |
| INVENTOR(S) | : Pierre Guedon | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Signed and Sealed this

Thirteenth Day of January, 2015

Michelle K. Lee
*Deputy Director of the United States Patent and Trademark Office*